United States Patent [19]
Bagaoisan et al.

[11] Patent Number: 6,126,634
[45] Date of Patent: Oct. 3, 2000

[54] BALLOON ASSEMBLY WITH SEPARATELY INFLATABLE SECTIONS

[75] Inventors: Celso Jacinto Bagaoisan, Newark; Ketan P. Muni, San Jose, both of Calif.

[73] Assignee: Advanced Cardiovascular Systems, Santa Clara, Calif.

[21] Appl. No.: 08/763,927

[22] Filed: Dec. 12, 1996

Related U.S. Application Data

[63] Continuation of application No. 08/592,241, Jan. 26, 1996, which is a continuation of application No. 08/321,002, Oct. 5, 1994, which is a continuation of application No. 07/917,812, Jul. 21, 1992, Pat. No. 5,415,635.

[51] Int. Cl.[7] ................................................ A61M 25/00
[52] U.S. Cl. ............................ 604/96; 604/101; 604/509; 606/191
[58] Field of Search ........................... 604/96–104, 500, 604/508, 509; 606/191–194

[56] References Cited

U.S. PATENT DOCUMENTS

| Re. 33,166 | 2/1990 | Samson | 606/194 |
|---|---|---|---|
| 2,892,458 | 6/1959 | Auzin | 128/349 |
| 4,323,071 | 4/1982 | Simpson et al. | 128/343 |
| 4,748,982 | 6/1988 | Horzewski et al. | 128/344 |
| 4,771,765 | 9/1988 | Choy et al. | 604/101 |
| 4,911,163 | 3/1990 | Fina | 606/127 |
| 4,990,139 | 2/1991 | Jang | 604/101 |
| 5,002,532 | 3/1991 | Gaiser et al. | 604/101 |
| 5,019,042 | 5/1991 | Sahota | 604/101 |
| 5,040,548 | 8/1991 | Yock | 128/898 |
| 5,061,273 | 10/1991 | Yock | 606/194 |
| 5,071,406 | 12/1991 | Jang | 604/96 |
| 5,074,845 | 12/1991 | Miraki et al. | 604/101 |
| 5,078,394 | 1/1992 | Keith | 204/22 |
| 5,163,906 | 11/1992 | Ahmadi | 604/101 |
| 5,176,638 | 1/1993 | Michael | 604/101 |
| 5,188,596 | 2/1993 | Condon et al. | 604/101 |
| 5,470,313 | 11/1995 | Crocker et al. | 604/96 |
| B1 4,323,071 | 5/1990 | Simpson et al. | 128/343 |

FOREIGN PATENT DOCUMENTS

| 0 197 787 A3 | 10/1986 | European Pat. Off. . |
| 0 512 359 A1 | 11/1992 | European Pat. Off. . |
| 0 540 858 A1 | 5/1993 | European Pat. Off. . |

*Primary Examiner*—John D. Yasko
*Attorney, Agent, or Firm*—Heller Ehrman White & McAuliffe LLP

[57] ABSTRACT

A dilatation or other similar catheter for intraluminal use which has an elongated shaft and an inflatable member or section on the distal extremity of the catheter shaft which has multiple working sections, a first working section which elastically expands upon inflation to a first pressure within a first pressure range and a second working section which elastically expands upon inflation to a second pressure within a second pressure range which is at least in part higher than the first pressure range. The first working section may be inflated to secure the catheter within the body lumen and then the second working section may be inflated to dilatate the body lumen.

2 Claims, 3 Drawing Sheets

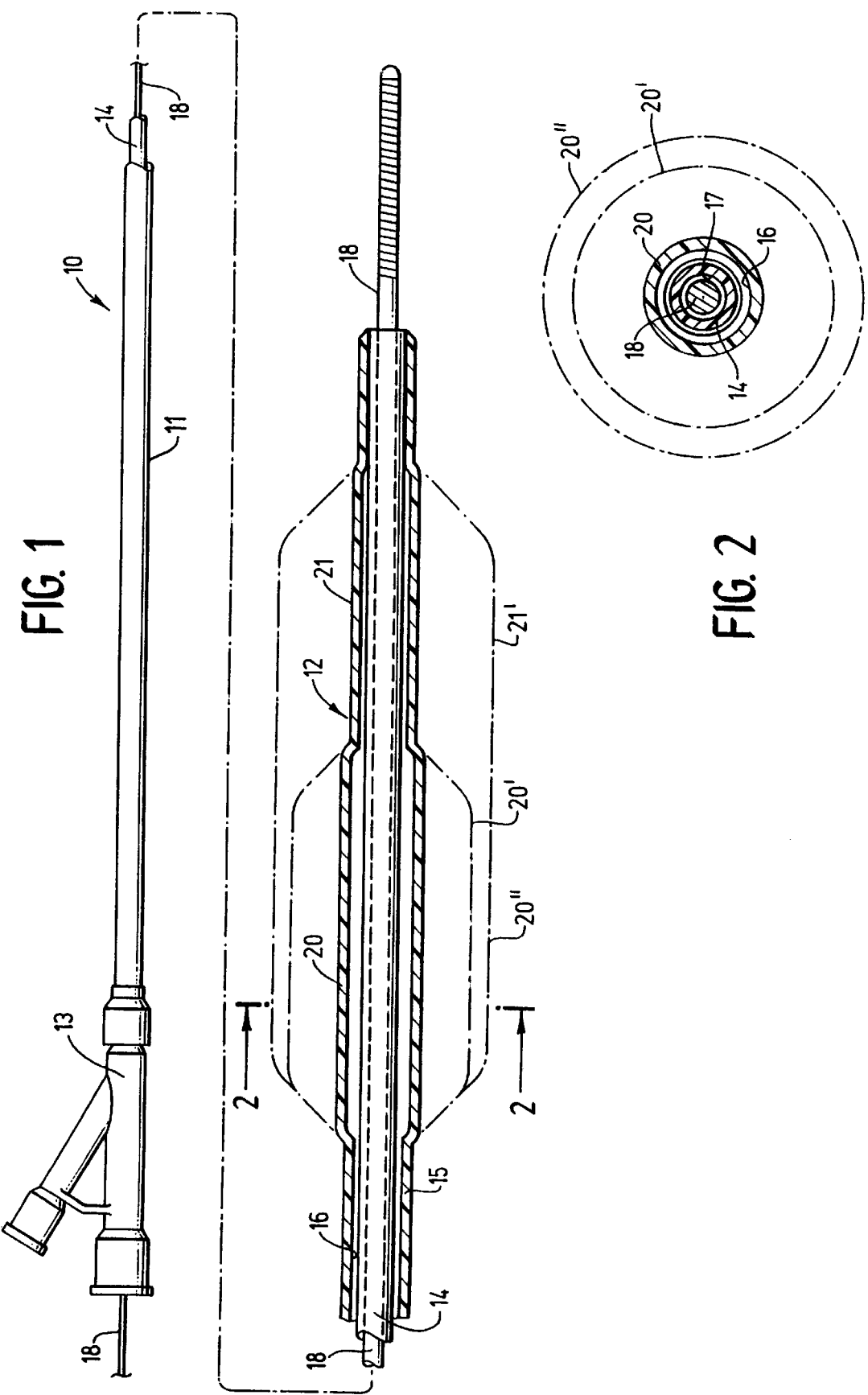

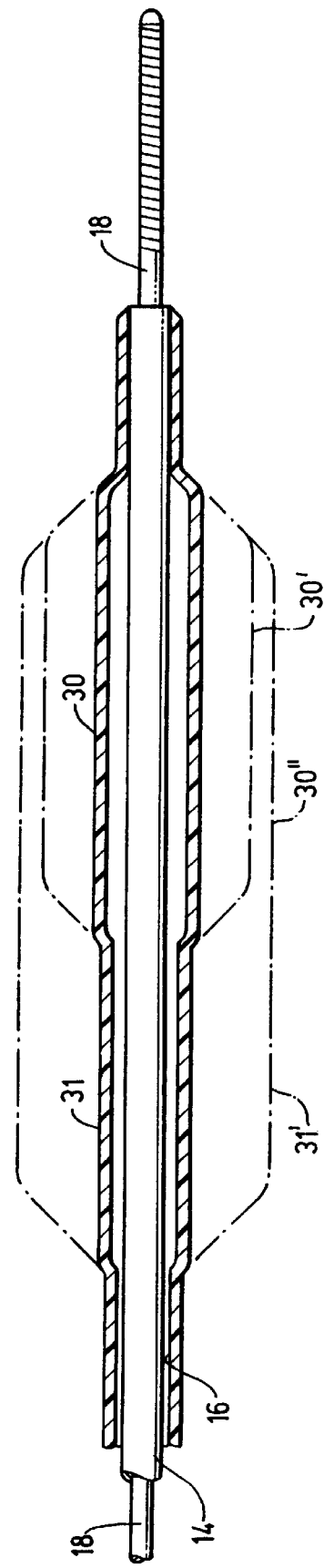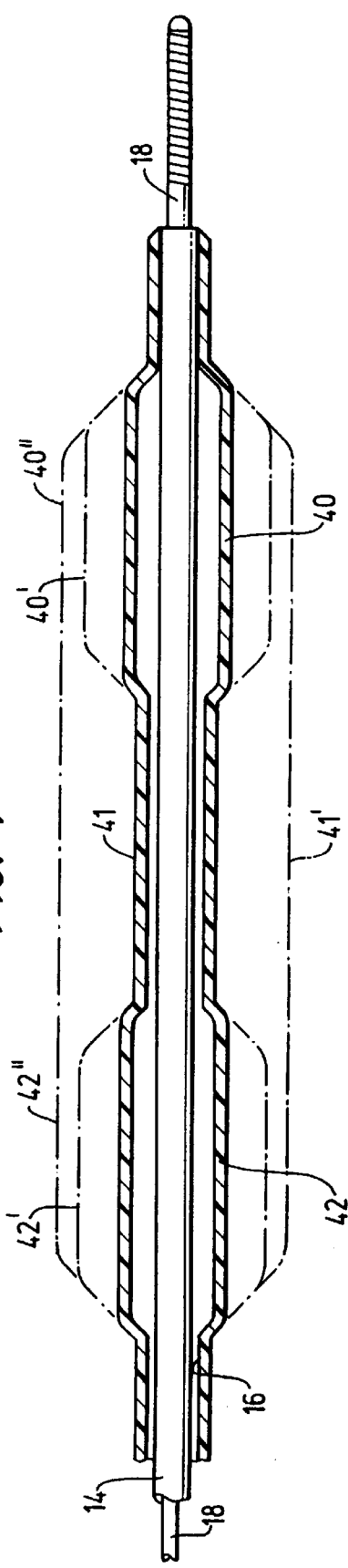

BALLOON ASSEMBLY WITH SEPARATELY INFLATABLE SECTIONS

This is a continuation of copending application Ser. No. 08/592,241, which was filed on Jan. 26, 1996, which is a continuation of Ser. No. 08/321,002, filed Oct. 5, 1994, which is a continuation of Ser. No. 07/917,812, filed Jul. 21, 1992, now U.S. Pat. No. 5,415,635.

BACKGROUND OF THE INVENTION

The present invention is directed to a balloon assembly for catheters which are suitable for intraluminal procedures such a percutaneous transluminal coronary angioplasty (PTCA).

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and increase the blood flow through the artery. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced therein until the preshaped distal tip of the guiding catheter is disposed within the aorta adjacent the ostium of the desired coronary artery. The guiding catheter is twisted or torqued from the proximal end, which extends out of the patient, to guide the distal tip of the guiding catheter into the ostium. A balloon dilatation catheter may then be advanced through the guiding catheter into the patient's coronary artery until the balloon on the catheter is disposed within the stenotic region of the patient's artery. The balloon is inflated to open up the arterial passageway.

One type of catheter frequently used in PTCA procedures is an over-the-wire type balloon dilatation catheter. Commercially available over-the-wire type dilatation catheters include the SIMPSON ULTRA-LOW PROFILE®, the HARTZLER ACX®, the HARTZLER ACX II™, the PINKERTON .018™ and the ACS TEN™ balloon dilatation catheters sold by the assignee of the present invention, Advanced Cardiovascular Systems, Inc. (ACS). Over-the-wire type dilatation catheters are described and claimed in U.S. Pat. No. 4,323,071 (Simpson-Robert) which is incorporated by reference into this application.

When using an over-the-wire dilatation catheter, a guidewire is usually inserted into an inner lumen of the dilatation catheter before it is introduced into the patient's vascular system and then both are introduced into, and advanced through, the guiding catheter to its distal tip which is seated within the ostium. The guidewire is first advanced out the seated distal tip of the guiding catheter into the desired coronary artery until the distal end of the guidewire extends beyond the lesion to be dilatated. The dilatation catheter is then advanced out of the distal tip of the guiding catheter into the patient's coronary artery, over the previously advanced guidewire, until the balloon on the distal extremity of the dilatation catheter is properly positioned across the lesion to be dilatated. Once properly positioned across the stenosis, the balloon is inflated one or more times to a predetermined size with radiopaque liquid at relatively high pressures (e.g., generally 4–12 atmospheres) to dilate the stenosed region of a diseased artery. After the inflations, the balloon is finally deflated so that the dilatation catheter can be removed from the dilatated stenosis to resume blood flow.

Fixed-wire type dilatation catheter systems are also utilized very frequently in PTCA procedures. This type of dilatation catheter has a guidewire or guiding member secured within the catheter and it provides low profiles, i.e. small transverse dimensions, because there is no inner tubular member which is characteristic of commercially available over-the-wire dilatation catheters. Commercially available fixed-wire dilatation catheters include the HARTZLER EXCEL®, the HARTZLER LPS® and the SLALOM™ dilatation catheters sold by ACS. Fixed-wire dilatation catheters are disclosed and claimed in U.S. Reissue 33,166 which is incorporated by reference into this application.

Another type of dilatation catheter, the rapid exchange type catheter, was introduced by ACS under the trademark ACS RX® Coronary Dilatation Catheter. It is described and claimed in U.S. Pat. No. 5,040,548 (Yock), U.S. Pat. No. 5,061,273 (Yock) and U.S. Pat. No. 4,748,982 (Horzewski, et al.) which are incorporated herein by reference. This dilatation catheter has a short guidewire receiving sleeve or inner lumen extending through a distal portion of the catheter. The sleeve or inner lumen extends proximally from a first guidewire port in the distal end of the catheter to a second guidewire port in the catheter spaced proximally from the inflatable member of the catheter. A slit may be provided in the wall of the catheter body which extends distally from the second guidewire port, preferably to a location proximal to the proximal end of the inflatable balloon. The structure of the catheter allows for the rapid exchange of the catheter without the need for an exchange wire or adding a guidewire extension to the proximal end of the guidewire. This catheter has been widely praised by the medical profession, and it has met with much success in the marketplace because of the advantages of its unique design.

The perfusion type dilatation catheter was another type of dilatation catheter first introduced into the marketplace by ACS. This catheter, which can take the form of an over-the-wire, fixed-wire or a rapid exchange type catheter, has one or more perfusion ports proximal to the dilatation balloon in fluid communication with the guidewire receiving inner lumen extending to the distal end of the catheter. A plurality of perfusion ports are preferably provided in the catheter distal to the balloon which are also in fluid communication with the inner lumen extending to the distal end of the catheter. When the balloon of this dilatation catheter is inflated to dilatate a stenosis, oxygenated blood in the artery or the aorta, or both, depending upon the location of the dilatation catheter within the coronary anatomy, is forced to pass through the proximal perfusion ports, through the inner lumen of the catheter, and out the distal perfusion ports. The catheter provides oxygenated blood downstream from the inflated balloon to thereby prevent or minimize ischemic conditions in tissue distal to the balloon. The perfusion of blood distal to the inflated balloon allows for long term dilatations, e.g. 30 minutes or even several hours or more. This catheter has likewise been highly praised by the medical profession and has met with much commercial success. Commercially available perfusion type dilatation catheters include the STACK PERFUSION® and the ACS RX PERFUSION™ dilatation catheters which are sold by ACS.

It is not uncommon with all types of dilatation catheters to have some difficulty in properly positioning the inflatable member or balloon on the distal ends of these catheters within the stenotic region of a patient's artery or other body lumen or, if properly positioned within the stenosis, to have difficulty in maintaining the position of the inflatable member or balloon within the stenosis during balloon inflation.

What is needed and has been previously unavailable is an inflatable member which can be preferentially inflated at different sections to better control the position of the inflatable member and to provide a more uniform pressure against the stenosis during the dilatation. The present invention satisfies these and other needs.

SUMMARY OF THE INVENTION

The present invention is directed to an improved inflatable assembly for intraluminal catheters such as are employed in PTCA and peripheral angioplasty.

The inflatable catheter portion of the present invention has at least two separately inflatable working sections, a first working section which upon inflation to a first pressure within a first pressure range expands substantially in an elastic mode and a second working section which upon inflation to a second pressure, higher than the first pressure within a second pressure range expands substantially in an elastic mode. The individual working sections of the inflatable member are considerably less compliant at pressures greater than the first and second pressure ranges respectively and exhibit much less expansion at pressures above the respective pressure ranges. Upon deflation, the working sections of the inflatable member preferably contract substantially by means of elastic recoil to provide very low deflated profiles. Preferably, the elastic expansion of the first working section is substantially complete before any significant amount of elastic expansion of the second working section occurs to allow the first working section to firmly secure the catheter within a body lumen before the second working section is inflated to any significant extent. In other embodiments, the complete inflation of the first working section before the initiation of inflating the second working section allows the first working section to predilate a stenosis so that the second working section can be advanced within the stenosis and then be inflated to a pressure within the second pressure range to complete the dilatation.

In one presently preferred embodiment, the first working section of the inflatable catheter section is proximal to the second working section, whereas, in another presently preferred embodiment the first working section is distal to the second working section. In a third embodiment, a variant of the first embodiment, a third working section, preferably having essentially the same characteristics as the first working section, may be provided distal to the second working section.

A dilatation catheter having a inflatable balloon assembly in accordance with the present invention generally has an elongated shaft with an inner lumen extending within the shaft which is in fluid communication with the interior of the inflatable working sections. The use of a single inflation lumen for delivery of inflation fluid to multiple inflatable members reduces considerably the profile of the catheter shaft.

A dilatation catheter having first and second inflatable members or sections of the invention may be advanced within a patient's arterial system in a conventional manner such as described in the BACKGROUND OF THE INVENTION until the second inflatable working section extends into the stenosis and the first inflatable working section of the balloon is disposed proximally adjacent to the stenosis. Inflation fluid is directed through the inner lumen of the catheter shaft into the interior of the first and second inflatable working sections at a first pressure level to expand the first inflatable working section to a diameter which secures the first working section within the artery. The pressure is increased to a second higher pressure level, which causes the second inflatable working section to expand to a diameter which dilatates the stenosis. Preferably, the first working section is expanded substantially before any significant expansion of the second working section occurs and during the dilatation of the stenosis, the dilatation catheter is held firmly in position within the artery by the expanded first working section. However, after inflating the first inflatable working section to the first diameter to secure the catheter within the artery, further increases in internal pressure to inflate the second inflatable working section to dilate the stenosis, do not significantly increase the diameter of the first inflatable working section. The elastic expansion of the second inflatable working section within the stenosis applies little or no shear stress to the stenosis, thereby minimizing the chances for a dissection of the stenosis which can interrupt blood flow through the artery and can hasten restenosis.

In one presently preferred embodiment of the invention the first inflatable working section is disposed within the artery proximal to stenosis while the second inflatable working section is disposed within the stenosis. In the second preferred embodiment, the first inflatable working section is disposed distal to the stenosis while the second inflatable working section is disposed within the stenosis. The first and second preferred embodiments may be utilized in essentially the same manner.

Use of the third embodiment provides for a firm fix of the inflatable section of the catheter on both sides of the stenosis by the inflation of the first and third working sections prior to the expansion of the second working section to dilate the stenosis.

The working sections of the balloon of the invention can be formed in a variety of ways to provide the desirable differential expansion. One presently preferred method is to extrude a tubular member of one or more polyolefinic ionomers, such as the sodium, lithium and zinc ionomers sold by E.I. duPont, deNemours & Co. under the trademark Surlyn®, and then to irradiate at least the portion of the extruded tubular member which is to be the inflatable portion to cross-link the polymer. Blends with other polymers such as polyethylene with the ionomers may also be employed. The portion of the tubular member which is to be formed into the second working section is given a heat treatment after the extrusion thereof within 50° C. of the crystalline melting point, whereas the portion of the tubular member which is to be formed into the first working section is given essentially the same heat treatment after the extrusion thereof but is also inflated to expand this portion of the balloon within the thermal treatment range. A tight fitting sheath or other suitable device is placed around the portion which forms the second working section of the inflatable section to prevent its expansion during the inflation of the first working section. After the expansion of the first working section, it is cooled and the expanded portion is heated to heat shrink the expanded section.

Other means can be employed to provide the separate expansion of the first and second working sections of the balloon. For example, the portion of the balloon which forms the first working section can formed from a portion of the tubular member which has a thinner wall than the portion which forms the second working section. Upon expansion of the balloon to a first pressure level the first working section with a thinner wall will expand to its working diameter before the second working section. The first and second inflatable working sections may be made of different materials to provide the same effects of inflating at different pressure levels. Providing different levels of irradiation of the inflatable sections may also be employed to generate differentials in material properties of the inflatable working sections by varying the cross-linking of the polymer material.

The inflatable portion of the catheter of the invention with separate expansion of multiple working sections allows the expansion of the first working section to firmly secure the inflatable member within the artery or other body lumen before significant the expansion of the second working section to apply pressure to the artery or other lumenal wall. Moreover, the second working section provides for the uniform application of radial pressure to the artery or body lumen without applying significant shear stress to the artery of body lumen wall, which can significantly reduce the risk of dissections during dilatations which can impede blood flow through the artery. The lower shear stresses can also reduce the incidence of restenosis which is common in over 30% of arterial dilatations.

The various inflatable working sections may also be designed to inflate to different diameters such as described in U.S. Pat. No. 5,002,532 which is incorporated by reference into this application. The most distal working section may be provided with a smaller inflated diameter and be used to predilate the stenosis at a first pressure so that the second working section can be subsequently advanced into the stenosis to be inflated and complete the dilatation.

Other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a dilatation catheter embodying features of the invention, FIG. 2 is a transverse cross-sectional view of the catheter shown in FIG. 1 taken along the lines 2—2.

FIG. 3 is an elevational view, partially in section, of the distal portion of an alternative embodiment of the invention.

FIG. 4 is an elevational view, partially in section, of the distal portion of another alternative embodiment of the invention.

DETAILED DESCRIPTION OF THE INVENTION

Figure 5:
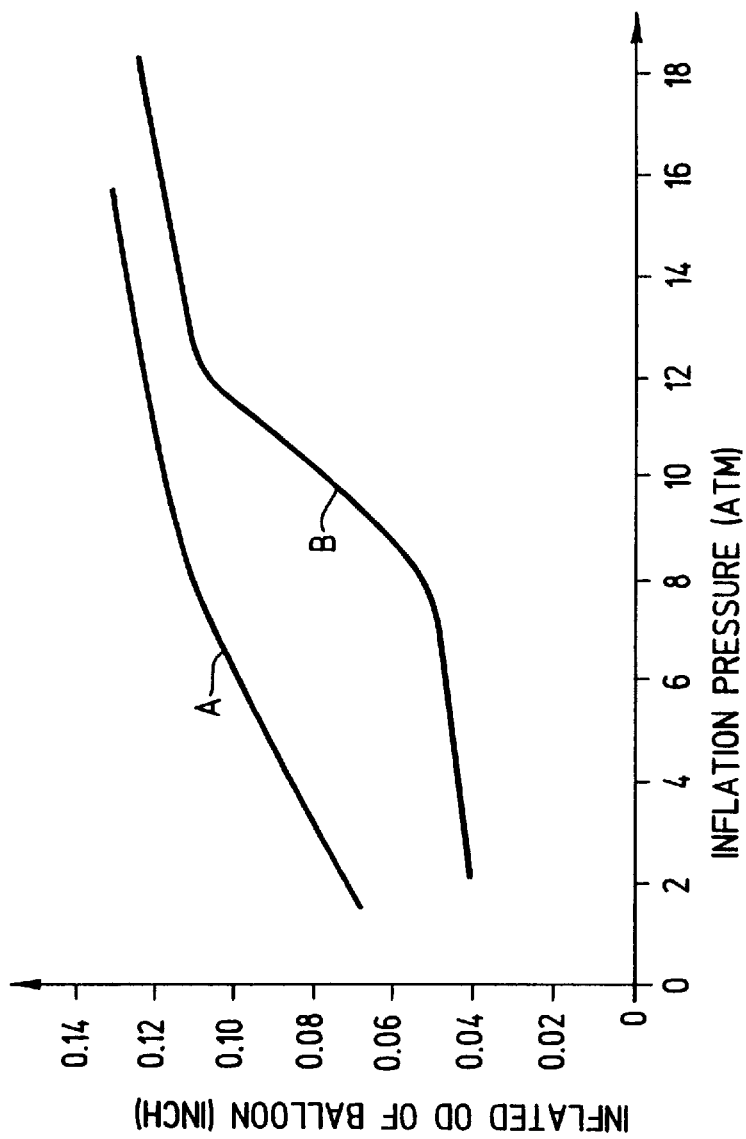
FIG. 5 is a graphical representation of the relationship between balloon diameter and inflation pressure for inflatable working sections of the invention.

FIGS. 1 and 2 schematically illustrate a dilatation catheter 10 embodying features of the invention which would be suitable for PTCA. The catheter 10 includes a catheter shaft 11, and inflatable section 12 on a distal portion of the catheter shaft and an adapter 13 on the proximal end of the catheter shaft. As shown, the catheter shaft 11 has an inner tubular member 14 and an outer tubular member 15 disposed concentrically about the inner tubular member and defining with the inner tubular member an annular inflation lumen 16. The inner tubular member 14 has an inner lumen 17 which is adapted to slidably receive a guidewire 18.

The inflatable section 12 has a first inflatable working section 20 which has an interior in fluid communication with the annular lumen 16 and which is adapted to inflate at pressures within a first pressure range and a second inflatable working section 21 which is also in fluid communication with the annular lumen 16 and which is adapted to inflate at pressures within a second pressure range which is at least in part greater than the first pressure range. The inflated profiles of the working sections 20 and 21 are shown in phantom in the drawings. During inflation the proximal working section 20 elastically expands to a first diameter within the first pressure range as shown by 20'. The distal working section 21 elastically expands to a second diameter within the second pressure range as shown by 21'. The expanded proximal working section 20' may expand slightly more when the inflation pressure is increased to inflate the second section as shown by 20". While the final inflated diameters of the first and second working sections 20 and 21 are shown in the drawing to be the same they need not be the same.

FIG. 3 depicts an alternative embodiment wherein the second working section 31 is proximal to the first working section 30. It is otherwise the same as the previously discussed embodiment. The utilization is essentially the same except that the first working section secures the inflatable member distal to the stenosis. The inflated shapes of the working sections 30 and 31 are shown in phantom by 30', 30" and 31'.

FIG. 4 illustrates an alternative embodiment which is a variant to the embodiment shown in FIGS. 1 and 2 wherein a third inflatable working section 40 is provided distal to the second working section 41. This construction allows the inflatable section to be secured within the lumen on both sides of the stenosis. The expansion of the third inflatable working section 40 within the first pressure range is shown in phantom at 40' and within the second higher pressure range is shown is phantom at 40". The expansions of the first expandable working section 42 is essentially the same as for the third working section 40 and is designated 42' and 42".

Figure 6:
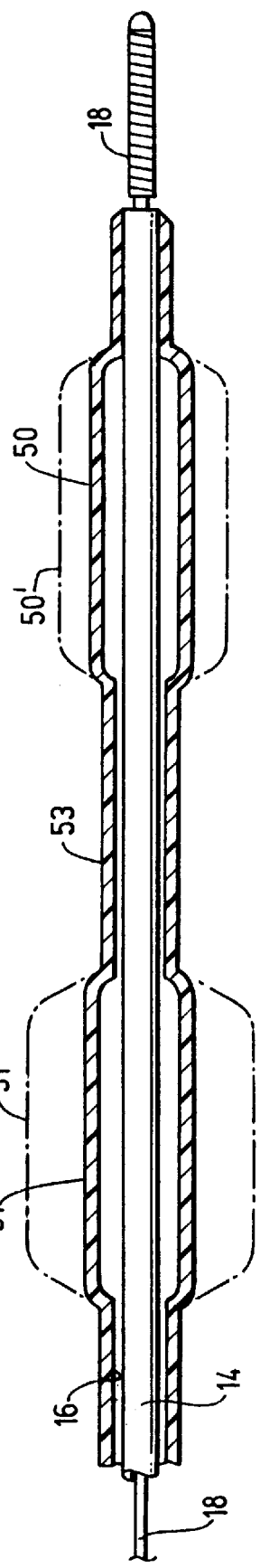
FIG. 6 is an elevational view, partially in section, of the distal portion of another alternative embodiment of the invention.

Another alternative embodiment is shown in FIG. 6. In this embodiment the first and second inflatable working sections 50 and 51 are separated by an essentially noninflatable portion 53. The other portions of the catheter are essentially the same as in the previous embodiments and are similarly numbered. In this catheter design the inflated diameter of the first working section, shown in phantom and designated 50', is smaller than the inflated diameter of the second working section shown in phantom and designated 51'. The first inflatable working section 50 may be utilized to predilate a stenosis and then the catheter can be advanced within the artery until the second inflatable working section 51 is disposed within the predilated stenosis and inflated to complete the dilation of the stenosis.

The dimensions of the dilatation catheters of the invention may be conventional. However, the length of the inflatable section of the catheter will generally be longer than conventional dilatation balloons. The first and third inflatable working sections of dilatation catheters for coronary angioplasty may be about 1 to about 5 cm in length, whereas the second working section may be about 1 to about 3 cm in length, which is about the length of conventional dilatation balloons for coronary angioplasty. Typical diameters for coronary angioplasty may range from about 1 to about 4 mm. Other lengths and diameters may be used. For example, for prostatic urethral dilatations the inflated diameter of the first working section may be in range of about 10 to about 30 mm.

A presently preferred inflatable member of the invention may be made by first extruding pellets of a zinc olefinic ionomer, identified as F1855 (a low molecular weight variant of 9020 Surlyn® from duPont, deNemours & Co.) at a temperature between about 350° F. to about 450° F. into tubular stock. Upon exiting from the extrusion die, the tubular stock is quenched in a trough of cool water and then stabilized at about 40° C. to 80° C., typically about 60° C. for about 2 to about 6 hours, typically about 4 hours. The stabilized tubular product is then irradiated. The portion of the tubular member which is to form the first working section is irradiated at about 5 to about 20 Mrads, preferably about 5 to abut 10 Mrads, and the portion which is to form the second working section is irradiated at about 40 to about 70 Mrads, preferably about 50 to about 60 Mrads. The portions of the tubular product which are to be formed into the working sections of the inflatable member are then heat treated at a temperature of about 225° F. to about 250° F. The portion of the tubular member which is to be the first working section is subjected to an internal pressure of about 50 to about 85 psi, preferably about 60 to about 75 psi, at the elevated temperature of the heat treatment to expand or blow this heat treated portion of the tubular member into a balloon which forms the first working section. The balloon is blown slightly larger than the desired inflated size, e.g. up to about 3.1 mm if an inflated diameter of 3.0 mm is desired. The balloon is blown within a capture or shaping tube to ensure that the desired balloon shape is obtained. After cooling, the blown balloon is heated to a temperature of about 55° C. to about 65° C. for about 10 to about 30 minutes to heat shrink the balloon to a diameter about the same or slightly larger than its original diameter to form the first inflatable working section. The unblown heat treated portion of the tubular member forms the second inflatable working section. Preferably, a heat shrinkable sheath is placed about the balloon during the heat treatment so as to form the small wings generated around the inner member to reduce the profile. Curve A found in FIG. 5 illustrates the relationship between the outer diameter of a inflatable working section of a balloon and the internal pressure of the inflation fluid when a working section has been treated as described above. As indicated, the expansion of the working section is directly related to pressure, i.e. elastic, up to about 9 atmospheres and after about 9 atmospheres the rate of expansion, while constant indicating elastic expansion, decreases considerably.

In another example, the same extruded and irradiated tubular product described above, which is formed of zinc olefinic ionomer, was treated by heat treating at about 225° F. to abut 250° F., but was not inflated at the elevated temperature nor heat shrunk as in the prior example. Curve B in FIG. 5 illustrates a typical relationship between the internal fluid pressure and the outer balloon diameter of inflatable members or balloons which have been formed in this manner. In this case, there is relatively little expansion of the inflatable member until the internal pressure exceeds about 7 atmospheres and then there is a substantial increase in the rate of expansion until the internal pressure reaches about 12 atmospheres. The expansion is elastic within this range. At about 12 atmospheres the rate of expansion of the inflatable member is reduced considerably over the rate of expansion found between about 7 and 12 atmospheres.

While the present invention has been described herein in terms of coronary dilatation catheters, those skilled in the art will recognize that the catheter of the invention can be utilized in a variety of situations such as in the dilatation of a prostatic urethra of a male patient to treat benign hyperplasia. In this latter instance the first working section, which inflates at the lower pressure, may be disposed distal to the second working section so that it can be inflated within the patient's bladder to position the catheter within the urethra at the first pressure and then the second inflatable working section is inflated to a second higher pressure to dilate the prostatic urethra.

A variety of modifications can be made to the present invention. For example, the inflatable member need not be formed from the catheter shaft but may be formed separately and be secured to the distal end of the catheter shaft. The inflatable working sections of the inflatable portion of the catheter may likewise be formed as separate inflatable members and then subsequently joined to the catheter shaft by suitable means such as an adhesive. Other modifications and improvements can be made to the invention without departing from the scope thereof.

What is claimed is:

1. A balloon dilatation catheter comprising:
    a) an elongated flexible catheter shaft having proximal and distal ends and an inflation lumen extending within the catheter shaft; and
    b) an inflatable balloon on a distal extremity of the catheter shaft having
        a first balloon section which is inflatable to a first diameter at a first pressure,
        a second balloon section which is inflatable to a second diameter larger than the diameter of the first balloon section at a second pressure higher than the first pressure, and
        an interior chamber which is defined at least in part by the first and second balloon sections and which is in fluid communication with the inflation lumen.

2. The balloon dilatation catheter of claim 1 wherein the catheter shaft has a guidewire port in the distal end thereof and a guidewire lumen extending through the catheter shaft to and in fluid communication with the guidewire port in the distal end of the catheter.

* * * * *